(12) United States Patent
Chen

(10) Patent No.: US 8,603,251 B2
(45) Date of Patent: Dec. 10, 2013

(54) METHOD FOR PREPARING MAIN HYDROLYSATE BY HYDROLYZING PLANT CELLULOSE MATERIALS WITH CONCENTRATED SULFURIC ACID

(76) Inventor: Peihao Chen, Dongguan (CN)

( * ) Notice: Subject to any disclaimer, the term of this patent is extended or adjusted under 35 U.S.C. 154(b) by 597 days.

(21) Appl. No.: 12/678,735

(22) PCT Filed: Jul. 29, 2008

(86) PCT No.: PCT/CN2008/071790
§ 371 (c)(1),
(2), (4) Date: Jun. 25, 2010

(87) PCT Pub. No.: WO2009/036673
PCT Pub. Date: Mar. 26, 2009

(65) Prior Publication Data
US 2010/0275908 A1 Nov. 4, 2010

(30) Foreign Application Priority Data
Sep. 18, 2007 (CN) .......................... 2007 1 0030294

(51) Int. Cl.
*C13K 1/02* (2006.01)
(52) U.S. Cl.
USPC .......................................................... 127/37
(58) Field of Classification Search
None
See application file for complete search history.

(56) References Cited

U.S. PATENT DOCUMENTS

| | | | |
|---|---|---|---|
| 3,116,975 A * | 1/1964 | Stein et al. | 423/448 |
| 3,932,209 A * | 1/1976 | Chatterjee | 162/157.6 |
| 2002/0148574 A1 * | 10/2002 | Van Draanen et al. | 162/14 |

FOREIGN PATENT DOCUMENTS

WO WO 9640970 * 12/1996

OTHER PUBLICATIONS

Peilin et al., "Study on the Hydrolytic Kinetics of Lignocellulose Material by Concentrated Sulfuric Acid," *Chemical Reaction Engineering and Technology* 9(1):34-41, 1993 (w/English translation).
Pingkai et al., "The Study on Hydrolysis Kinetics of Lignocellulosic Material with Concentrated Acids," *Chemistry and Industry of Forest Products* 13(1):77-82, 1993 (w/English translation).
Xiaohan et al., "The Study of Corn Stover Hydrolyzed by Concentrated Sulfuric Acid," *China Resources Comprehensive Utilization* 11:9-11, 2003 (w/English translation).

* cited by examiner

*Primary Examiner* — Bijay Saha
(74) *Attorney, Agent, or Firm* — Shimokaji & Associates P.C.

(57) ABSTRACT

The present invention relates to a method to dispose plant cellulose materials, in particular to a method for preparing a main hydrolysate by hydrolyzing the plant cellulose materials with concentrated sulfuric acid. The plant cellulose materials are mixed with sulfuric acid in batches, and the main hydrolysate is obtained after hydrolysis. The batch mixing includes the following procedures: (1) sulfuric acid solution is used to dissolve part of the plant cellulose materials thereby forming a hydrolysate; (2) when the plant cellulose materials can not be dissolved any more, concentrated sulfuric acid with the concentration more than 80 wt % is successively added into the hydrolysate, and another part of the plant cellulose materials are added; (3) and then the procedure as step (2) is repeated until all the plant cellulose materials are completely hydrolyzed. The method utilizing concentrated sulfuric acid to prepare the main hydrolysate can hydrolyze the maximum cellulose with the least sulfuric acid, thereby decreasing the acid recovery cost proportioned by per kilogram sugar obtained by hydrolysis.

11 Claims, No Drawings

METHOD FOR PREPARING MAIN HYDROLYSATE BY HYDROLYZING PLANT CELLULOSE MATERIALS WITH CONCENTRATED SULFURIC ACID

FIELD OF THE INVENTION

The present invention relates to a method to dispose plant cellulose materials, and more particularly to a method for preparing main hydrolysate by hydrolyzing the plant cellulose materials with concentrated sulfuric acid.

BACKGROUND OF THE INVENTION

It would ease the problem of the fossil energy resource, such as the petroleum depletion by using renewable resources, such as cellulose, to produce liquid fuel and chemical products. The technology of using cellulose to produce liquid fuel and chemical products comprises steps of hydrolyzing cellulose to form a carbohydrate, such as an oligosaccharide or a monosaccharide, and fermenting the carbohydrate to produce liquid fuel and chemical products by using microorganisms. Typically, methods of hydrolyzing the cellulose to form sugars include dilute acid method, concentrated acid method and enzyme method; therein the concentrated acid hydrolysis method has advantages of low reaction temperature, high yields, and little sideproducts, and a disadvantage of high cost of acid recovery.

The process of concentrated acid hydrolysis of cellulose mainly comprised of two procedures: ① main hydrolysis process of hydrolyzing cellulose to oligosaccharides in concentrated acid, thereby obtaining main hydrolysate; and ② posthydrolysis process of hydrolyzing the oligosaccharides to glucose, thereby obtaining post-hydrolysate.

A common advanced process of concentrated sulfuric acid hydrolysis of cellulose is a low-temperature and two-stage sulfuric acid hydrolysis process. The process mainly includes firstly hydrolyzing hemicellulose of the plant cellulose materials to form monosaccharides which contain pentaglucose as a main component by using dilute sulfuric acid, secondly dissolving and hydrolyzing residual cellulose to oligosaccharides, for example cellotetrose and the like, by using 65-80 wt % sulfuric acid solution, and diluting and heating the resulting hydrolysate for a period of time to hydrolyze the oligosaccharide to glucose.

The concrete process of concentrated acid hydrolysis, such as the ARKANSAS University process described in U.S. Pat. No. 4,608,245 to Clausen et al. is described to include the following steps: mixing cellulosic material with 70-72 wt % sulfuric acid at a temperature of 50° C. for 10 minutes, and keeping the ratio of the sulfuric acid to the cellulose above 7.2; diluting the acid with water till the concentration thereof is between 40-50 wt %, and incubating at 90° C. for 20 minutes; separating lignin from the hydrolysate; performing a first extraction on the cooled hydrolysate by using a first extractant of $C_4$-$C_7$ alkanols, such as heptanol, thereby obtaining an glucose-rich extraction raffinate and a first extract rich in sulfuric acid and the first extractant; then performing a second extraction to the first extract by using a second extractant of benzene, $CCl_4$ or toluene, thereby obtaining an extraction raffinate merely containing water and sulfuric acid and an extract merely containing the first and the second extractants; then separating the first extractant from the second extractant by using a method of reduced pressure distillation to recycle the recovered acid, the first and the second extractants; finally, neutralizing remaining amount of sulfuric acid with lime, and filtering to obtain a liquid glucose without sulfuric acid. The most original of the process is using extraction method to separate sugars from acids. This principle seems to be very prefect. It's contemplated, however, that the technology has no practicability after a brief analysis. According to the preferable embodiment of the patent, the compositions of the hydrolysate obtained from the posthydrolysis process include 55% sulfuric acid, 40.5% water and 4.5% sugars, that is, the ratio of the sulfuric acid to the sugars is equal to 12.2. The compositions of the first extract include 79.4% heptanol, 14.5% sulfuric acid, 5.3% water and trace amount of sugars, that is, the ratio of the heptanol to the sulfuric acid is equal to 5.5. In the second extraction, the ratio of benzene to heptanol is about 5, that is, the quantity of benzene required to evaporate is 12.2×5.5× 5=335.5 kg, and the quantity of heat wasted is 335.5 kg×434 kJ/kg=145607 kJ. However, complete oxidation of 1 kg glucose yields energy of only 15945 kJ, which is much smaller than the quantity of heat needed for evaporating the benzene. Obviously, it is a process without practicability, whose energy output is much smaller than the input.

It is obvious that, in the current concentrated sulfuric acid hydrolysis process, concentrated sulfuric acid solution with a concentration of 65-80 wt % is made one-off reaction with the cellulose materials. To ensure a substantial hydrolysis of the dissolved cellulose to monosaccharide in a complete hydrolysis process (namely the main hydrolysis process and the posthydrolysis process), the weight of cellulose hydrolysable per unit weight of sulfuric acid is very small (namely the weight ratio of the cellulose to the sulfuric acid is small), causing the costs of acid recovery too high for per kilogram of sugar obtained by hydrolysis. Furthermore, the water content of the main hydrolysate is higher. Moreover, it brings difficulty to recover the acid from the post-hydrolysate, thereby restricting the applications of the concentrated sulfuric acid hydrolysis that includes a lot of advantages.

SUMMARY OF THE INVENTION

To overcome the above-mentioned drawbacks, the present invention is aimed at providing a method for preparing main hydrolysate by hydrolyzing plant cellulose materials with concentrated sulfuric acid, so as to obtain a main hydrolysate with lower water content, which is beneficial to recycle the sulfuric acid from the hydrolysate. Moreover, the hydrolysis method of the present invention can greatly increase and maximize the ratio of the cellulose to the sulfuric acid.

The method for preparing main hydrolysate by hydrolyzing plant cellulose materials with concentrated sulfuric acid comprising steps of:

(1) dissolving part of the plant cellulose materials by sulfuric acid solution thereby forming a first hydrolysate;

(2) adding concentrated sulfur acid with a concentration more than 80 wt % into the first hydrolysate when the sulfuric acid in the first hydrolysate can not dissolve the plant cellulose materials any more, and then adding another part of the plant cellulose materials thereby forming a second hydrolysate; and (3) repeating the step (2) when the sulfuric acid in the second hydrolysate can not dissolve the plant cellulose materials any more, until all the plant cellulose materials are completely hydrolyzed thereby obtaining a main hydrolysate.

Preferably, the concentration of the sulfuric acid solution in step (1) is 72-80 wt %. The concentration of the concentrated sulfuric acid in steps (2) and (3) is preferably 90-98 wt %.

In steps (2) and (3), the concentrated sulfuric acid is added to keep its concentration in the hydrolysate below 80 wt %.

The quantity of the sulfuric acid added in the last time in step (3) is such that the concentration of the sulfuric acid in the hydrolysate is not less than 60 wt %.

The method of the present invention is accomplished at a temperature between room temperature and 80° C., preferably at a temperature of 30-40° C. The stepwise addition of the concentrated sulfuric acid will result in a heat release during dilution of the acid, thus a reaction temperature between 30-40° C. can be achieved without additional heat input even the process is carried out at room temperature. When the main hydrolysis is accomplished at a temperature below 45° C., the main hydrolysate is incubated at a temperature between 45-55° C. for 5-20 minutes after all the metrical cellulose materials and sulfuric acid are added, such that the dissolved cellulose can be hydrolyzed to soluble glucose polymer which is soluble in water and easy to be hydrolyzed by diluted acid to monosaccharide. Otherwise, a higher amount of insoluble glucose polymer will be formed, which is insoluble in water and difficult to be hydrolyzed by diluted acid to form monosaccharide and, in turn, decreasing the yields. A main hydrolysate mainly containing oligosaccharide will be obtained after the main hydrolysis is accomplished.

In the method of the present invention, the plant cellulose materials are any materials containing cellulose, preferably, the plant cellulose materials pretreated to remove hemicellulose, and more preferably, the plant cellulose materials pretreated to remove hemicellulose and partial lignin and in a form of single fibre, namely unicellular state. On one hand, pentose which forms the hemicellulose is easy to decompose in concentrated acid, making the yield decreased. On the other hand, cellulose material in the unicellular state has a maximum contact area with the acid, thus the time of acid penetration is shortened, and the dissolution rate of the cellulose is improved significantly and, in turn, the decomposition of the sugars in the concentrated acid condition decreased (hydrolysis of the cellulose and the decomposition of the sugars always are concomitant in the concentrated acid condition). Thus, the yields of the sugars are increased.

In the method of the present invention, the water content of the plant cellulose materials is between 10-15 wt %, preferably 10 wt %.

In the method of the present invention, the sulfuric acid mixes and reacts with the plant cellulose materials in batches. By using the dissolved and hydrolyzed cellulose to dilute the batch-wisely added concentrated sulfuric acid, it can achieve the aim of dissolving and hydrolyzing the maximum cellulose with the least sulfuric acid, thereby decreasing the costs of acid recovery for per kilogram sugar obtained by hydrolysis. The water content of the main hydrolysate obtained by the present invention is less, which is beneficial to the subsequent acid recovery and the separation of the sugars.

Acid recovery is crucial to commercialize the methods of the concentrated sulfuric acid hydrolysis of cellulose. Decreasing the cost for the acid recovery has being a radical issue. Thus, it's desired to dissolve and hydrolyze the cellulose as much as possible by unit weight of sulfuric acid, in order to minimize the cost of acid recovery for unit weight of the sugars. It's known that, the cellulose can dissolve and perform a homogeneous hydrolysis in a 65-80 wt % sulfuric acid. Sulfuric acid with a concentration of 80-100 wt % can dissolve and hydrolyze the cellulose, however, saccharides undergo a fast charring due to the high acidity of the hydrolysate. The yield of the monosaccharide is thus decreased. Typically, sulfuric acid with such a high concentration won't be utilized to perform a hydrolysis. However, it's obvious that, the higher concentration of the sulfuric acid is, the more cellulose can be dissolved and hydrolyzed. Therefore, it is desirable to prepare a part of sulfuric acid solution at the beginning, and then add a certain quantity of cellulose material; add additional part of concentrated sulfuric acid when the hydrolysis is difficult to continue (ensuring the concentration of sulfuric acid of the hydrolysate being less than 80 wt % to prevent the sugars from charring), so as to dissolve additional cellulose material. Repeat such a procedure of adding cellulose and concentrated sulfuric acid, until all the predetermined quantity of cellulose material and concentrated sulfuric acid are added. The quantity of concentrated sulfuric acid added in the last batch should make the concentration of the sulfuric acid in the hydrolysate not less than about 60 wt %, to ensure the dissolved cellulose can be hydrolyzed to form maximum soluble glucose polymer. The insoluble glucose polymer is difficult to be hydrolyzed in the dilute acid condition of posthydrolysis. The quantity of the cellulose able to be dissolved and hydrolyzed by a certain quantity of the sulfuric acid will be decreased if more insoluble glucose polymer is produced. In fact, this is a method of adding acids step by step. The concentrated sulfuric acid used in the present invention has a concentration of, for example, 90-98 wt %, other than the currently utilized 65-80 wt %, thus, the water content of the hydrolysate is much less than that of the current hydrolysate. It is considered that, the material of diluting the concentrated sulfuric acid is the dissolved cellulose and the oligosaccharide obtained from hydrolysis, not the water, thereby preventing the quantity of cellulose dissolved and hydrolyzed by a certain quantity of the sulfuric acid from being decreased. In other words, it can increase the quantity of the cellulose dissolved and hydrolyzed by a certain quantity of sulfuric acid. According to the method of stepwise acid addition, the water introduced into the method will be reduced as long as the amount of the sulfuric acid used in step (1) is decreased and/or the concentration of sulfuric acid added subsequently is higher. Thus, a much higher quantity of the cellulose being dissolved and hydrolyzed by a certain quantity of sulfuric acid can be obtained. That is, the ratio of the cellulose to the sulfuric acid trends to the maximum.

The following description of the present invention will be presented in combination with several preferable embodiments. It is not intended to be exhaustive or limit the invention to the precise form disclosed, and obviously many modifications and variations are possible in light of the above teaching. Such modifications and variations that may be apparent to those skilled in the art are intended to be included within the scope of this invention as defined by the accompanying claims.

DETAILED DESCRIPTION OF ILLUSTRATED EMBODIMENTS

Embodiment 1

Cotton is the most pure cellulose material in the nature, and is unicellular, namely single fibrous plant cellulose material, which contains no hemicellulose, thereby being the standard material for testing.

15.9 grams 98 wt % sulfuric acid is prepared in order to hydrolyze 9.4 grams cotton (water content: 10%). Firstly, 30% of the above-mentioned 15.9 grams 98 wt % sulfuric acid, namely 4.8 grams 98 wt % sulfuric acid is added to 1.1 grams water to prepare an 80 wt % sulfuric acid solution serving as an initial hydrolysate. Then, the initial hydrolysate is cooled to room temperature. About 1 gram of the above-mentioned cotton is added to the initial hydrolysate, stirred and dissolved at room temperature so as to obtain an azury hydrolysate in which the concentration of the sulfuric acid becomes about 68 wt %. To the azury hydrolysate is added about 1 gram of 98 wt % sulfuric acid and stirred uniformly, so that the concentration of the sulfuric acid is increased to about 72 wt %. Then, about 1 gram of the above-mentioned cotton is added again and dissolved therein. Such a procedure of adding 98 wt % sulfuric acid and cotton is repeated until all of 15.9 grams of 98 wt % sulfuric acid and 9.4 grams of cotton have been added. Then, the hydrolysate is incubated at a temperature of 48-50° C. in a water bath for 8 minutes, to obtain 26.4 grams of a beige main hydrolysate with an acid concentration of 60 wt % and a water-soluble oligosaccharide concentration of 32 wt %. The ratio of the cellulose to the sulfuric acid of the present embodiment is 0.54, while the ratio of the cellulose to the sulfuric acid of a common technology is less than 0.14. Thus, in the method of sulfuric acid hydrolysis of cellulose of the present invention, the quantity of the sulfuric acid needed by a unit weight of cellulose is decreased significantly and, in turn, the cost of the acid recovery is decreased.

Embodiment 2

The present embodiment uses Bolboschoenus planiculmis as the plant cellulose materials, which has been pretreated to remove the hemicellulose and part of lignin, and substantially in the form of single fibre.

16.5 grams 98 wt % sulfuric acid is prepared in order to hydrolyze 10.6 grams Bolboschoenus planiculmis (water content: 13%). Firstly, 19% of the above-mentioned 16.5 grams 98 wt % sulfuric acid, namely 3.1 grams 98 wt % sulfuric acid is added to 1.1 grams water to prepare a 72 wt % sulfuric acid solution serving as an initial hydrolysate. Then, the initial hydrolysate is cooled to room temperature. About 1 gram of the above-mentioned Bolboschoenus planiculmis is added to the initial hydrolysate, stirred and dissolved at room temperature so as to obtain a puce hydrolysate. To the puce hydrolysate is added about 1 gram of 98 wt % sulfuric acid and stirred uniformly. Then, about 1 gram of the above-mentioned Bolboschoenus planiculmis is added again and dissolved therein. Such a procedure of adding 98 wt % sulfuric acid and Bolboschoenus planiculmis is repeated until all of 16.5 grams of 98 wt % metrical sulfuric acid and 10.6 grams of Bolboschoenus planiculmis have been added. Then, the hydrolysate is incubated at a temperature of 48-50° C. in a water bath for 8 minutes, to obtain a puce main hydrolysate containing the water-soluble oligosaccharide.

Embodiment 3

13.8 grams of water is added to 26.4 grams of main hydrolysate of the embodiment 1, to obtain a concentration of the sulfuric acid of about 40 wt %. And then, the resulting solution is incubated at a temperature of 75° C. in a water bath for 75 minutes thereby obtaining 40.2 grams of a puce post-hydrolysate. The post-hydrolysate is measured to contain 8.2 grams of reducing sugars, which is 91.4% of the theoretical yields. It's indicated that the oligosaccharide of the main hydrolysate obtained from the embodiment 1 is a soluble oligosaccharide which is easily hydrolyzed to monosaccharide in a diluted acid.

From the above-mentioned embodiments, it can be seen that, in the present method of producing main hydrolysate by hydrolyzing concentrated sulfuric acid with plant cellulose materials, the water content of the obtained hydrolysate is decreased greatly due to the stepwise acid addition. The ratio of the cellulose to the sulfuric acid is thus larger, which results in a reduction in the quantity of the acid needed, and accordingly, a significant decrease in the cost of acid recovery.

What is claimed is:

1. A method for preparing a main hydrolysate by hydrolyzing plant cellulose materials with concentrated sulfuric acid, the method comprising:
   (1) dissolving a portion of the plant cellulose materials in a sulfuric acid solution to form a first hydrolysate;
   (2) adding an amount of concentrated sulfuric acid having a concentration of more than 80 wt % into the first hydrolysate when the sulfuric acid in the first hydrolysate can no longer dissolve the plant cellulose materials, and adding another portion of the plant cellulose materials to form a second hydrolysate; and
   (3) repeating step (2) when the sulfuric acid in the second hydrolysate can no longer dissolve the plant cellulose materials until all the plant cellulose materials are completely hydrolyzed, thereby obtaining the main hydrolysate.

2. The method of claim 1, wherein the concentration of the sulfuric acid solution in step (1) ranges from 72 wt % to 80 wt %.

3. The method of claim 1, wherein the concentration of the concentrated sulfuric acid in steps (2) and (3) ranges from 90 wt % to 98 wt %.

4. The method of claim 1, wherein the amount of concentrated sulfuric acid added in steps (2) and (3) is such that the total concentration of sulfuric acid in the second hydrolysate is maintained below 80%.

5. The method of claim 1, wherein the amount of concentrated sulfuric acid added in step (3) is such that the total concentration of sulfuric acid in the main hydrolysate is not less than 60 wt %.

6. The method of claim 1, wherein the main hydrolysate is prepared at temperatures ranging from room temperature to 80° C.

7. The method of claim 1, wherein the main hydrolysate is prepared at a temperature below 45° C., and the main hydrolysate is incubated at a temperature ranging from 45° C. to 55° C. for a period of time ranging from 5 minutes to 20 minutes after all the cellulose materials and sulfuric acid are added.

8. The method of claim 1, wherein the plant cellulose materials are any materials containing cellulose.

9. The method of claim 1, wherein the plant cellulose materials are plant cellulose materials pretreated to remove hemicellulose.

10. The method of claim 1, wherein the plant cellulose materials are plant cellulose materials pretreated to remove hemicellulose and partial lignin and are in the form of a single fibre.

11. The method of claim 1, wherein a water content of the plant cellulose materials ranges from 10 wt % to 15 wt %.

* * * * *